United States Patent [19]

Belenger et al.

[11] Patent Number: 4,507,048
[45] Date of Patent: Mar. 26, 1985

[54] CENTRIFUGAL CLINICAL BLOOD PUMP

[76] Inventors: Jacques Belenger, 10, Rue Centrale, 1248 Geneva, Switzerland; Alain Jeanjacquot, 74560 Monnetier-Mornex, France

[21] Appl. No.: 347,041

[22] Filed: Feb. 8, 1982

Related U.S. Application Data

[63] Continuation-in-part of Ser. No. 124,222, Feb. 25, 1980, abandoned.

[30] Foreign Application Priority Data

Mar. 16, 1979 [FR] France .................... 79 07699

[51] Int. Cl.³ ............................................. F04D 29/22
[52] U.S. Cl. ............................... 415/90; 415/DIG. 4
[58] Field of Search ................. 415/10, 131, 170 R, 415/203, DIG. 4, 213 R; 416/3; 417/420; 308/166

[56] References Cited

U.S. PATENT DOCUMENTS

| 1,384,775 | 7/1921 | Pflueger | 308/166 |
| 1,577,110 | 3/1926 | Collins | 415/213 R |
| 2,326,180 | 8/1943 | Stempel | 308/166 X |
| 2,569,563 | 10/1951 | Grantham | 415/90 |
| 3,411,450 | 11/1968 | Clifton | 417/420 |
| 3,957,389 | 5/1976 | Rafferty et al. | 415/90 X |
| 4,013,384 | 3/1977 | Oikawa | 417/420 X |
| 4,036,565 | 7/1977 | Becker | 417/420 |
| 4,036,584 | 7/1977 | Glass | 415/90 |

FOREIGN PATENT DOCUMENTS 1383811 2/1975 United Kingdom ......... 415/DIG. 4

Primary Examiner—Robert E. Garrett
Assistant Examiner—Joseph M. Pitko
Attorney, Agent, or Firm—Robert E. Burns; Emmanuel J. Lobato; Bruce L. Adams

[57] ABSTRACT

A centrifugal clinical blood pump comprises a bell-shape or conical housing with a suction inlet at the apex and a tangential outlet adjacent the base. A conical rotator comprising at least one downwardly outflaring skirt surrounding a central cone is rotatably mounted in the housing by a jewelled pivot at the center of the base and a jewelled pivot mounted in the apex of the housing by a spider which is streamlined to permit free flow of fluid through the inlet into the pump housing. The jewelled pivots comprise a pointed shaft received in a recess of a jewel bearing or a single ball between two recessed jewel bearings. The rotator is driven by spaced permanent magnets embedded in the base of the rotator and an externally generated rotating magnetic field.

11 Claims, 9 Drawing Figures

Fig. 4
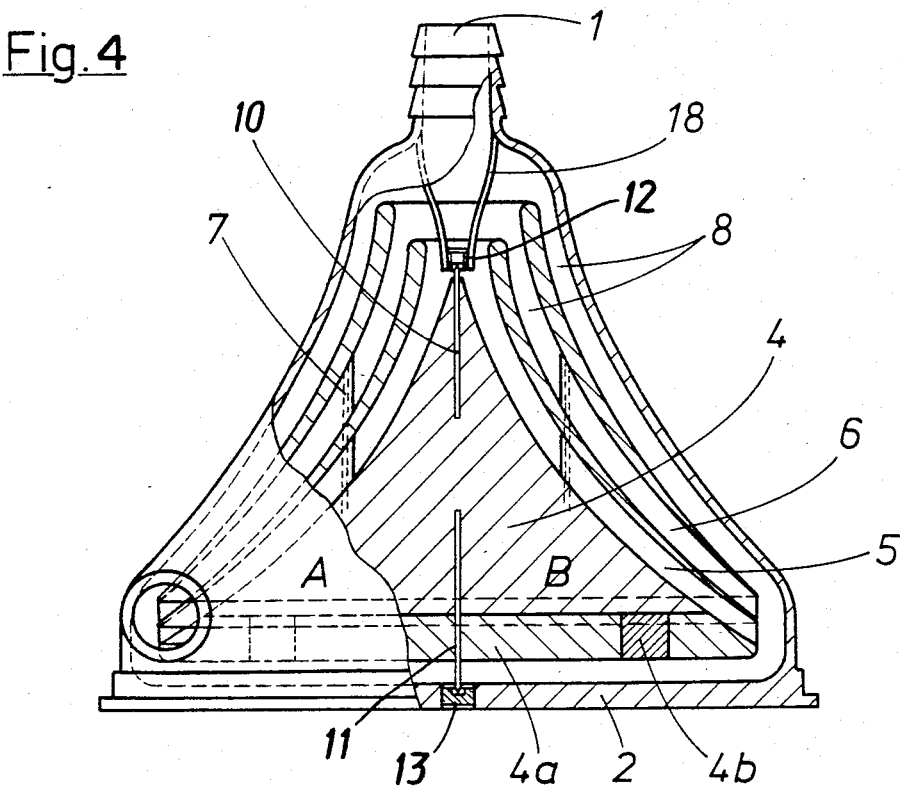
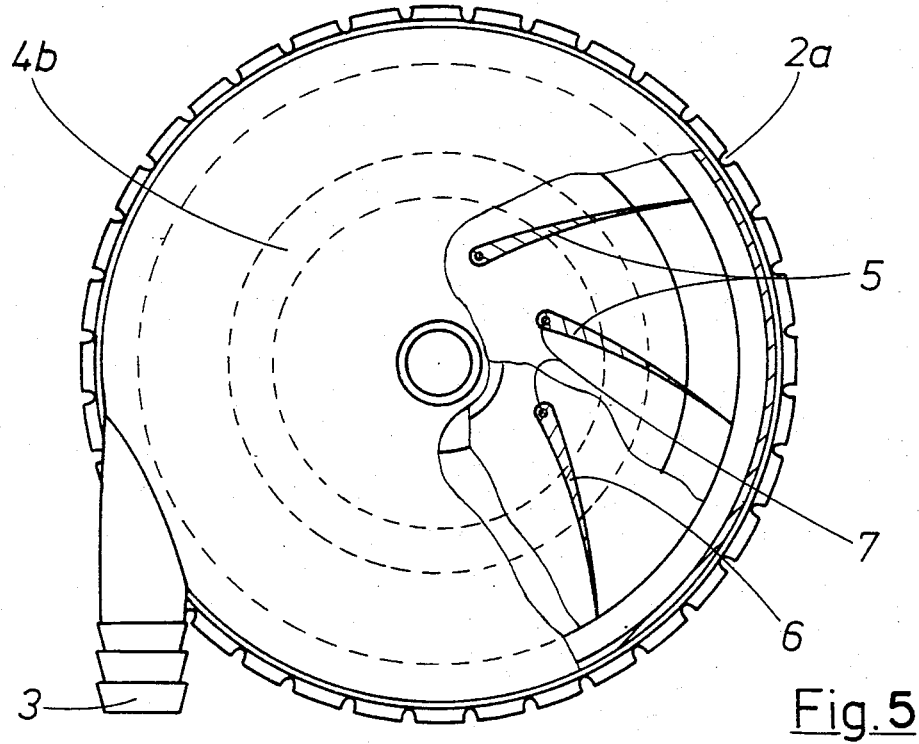
Fig. 5

CENTRIFUGAL CLINICAL BLOOD PUMP

REFERENCE TO PRIOR APPLICATION

This application is a continuation-in-part of our application Ser. No. 124,222 filed Feb. 25, 1980, now abandoned.

FIELD OF INVENTION

This invention relates in general to indirectly driven pumps, notably centrifugal pumps, intended for clinical use and especially for pumping blood in a living animal or man, replacing partially or totally the heart action, the pump being used as an external or as an implanted device. Pumps in accordance with the invention are primarily designed for pumping blood but they may be employed for other liquids and especially biological fluids or proteineous fluids susceptible of coagulation and degradation of proteic chains by heating.

BACKGROUND OF INVENTION

The handling of biological fluids must meet severe requirements. In particular the operation of the pump must be free of detrimental effects on the fluid handles or on the man or animal connected to the pump.

These detrimental effects are of several types:
(a) destruction of the formed elements of the blood by shear stress;
(b) induced coagulation;
(c) alteration of the proteins and other biochemical molecules of the fluid.

In centrifugal pumps the last two effects result mainly from heating problems.

Detrimental effects on the patient are embolization of coagulated blood, particles of seals, release or toxic products by the burning of the seal, alteration of circulating proteins. These effects may lead to nonreversible loss of function of the individual.

Prior centrifugal pumps for clinical use are driven indirectly but despite this fact they have frictional bearing seals which have been found to result in significant heat generation and potential degradation of the seals which lead to the detrimental effects referred to above.

Centrifugal pumps for clinical use have a conical shape with an axial suction inlet at the top of the cone and a radial or tangential outlet at the bottom of the pump. The rotator is also conical and comprises blades disposed at regular spaced radii or conical supporting coaxial bell-shaped elements revolving bodily with the rotator. Both types of rotator drive the fluid by viscosity effect.

The conical rotator incorporates a magnetic disc at its base or is solid with a magnetic disc located in a separate chamber, the pumping and magnetic chambers being separated by a partition which also serves as a friction bearing for the axle supporting the rotator. The magnetic chamber is permanently cooled by a continuous flow of cold liquid to ensure cooling of the axle and of the seal and, moreover, this liquid avoids penetration of blood into the magnetic chamber.

In another realization the rotator is rotatably mounted on the base of the housing on a shaft with seals on the housing side and on the rotator side of which the latter is a friction bearing.

In all of these realizations the friction bearings or friction seals not only generate heat but create a hot spot with a temperature high enough to cause blood coagulation. As a result of this none of the prior pumps is suitable for long term use and for intracorporeal implantation. On the other hand, for short term use the general tendency is to use devices for only one procedure so that the high cost of construction of prior pumps is disadvantageous.

SUMMARY OF THE INVENTION

It is an object of the present invention to improve the safety of use, the mechanical operation, the haemodynamical properties and in particular to reduce heat dissipation of pumps designed for circulating blood or other body fluids. While simplifying their construction and thus reducing their cost, the present invention renders the pumps suitable for long term use and hence for intrabody implantation.

In accordance with the invention a clinical centrifugal pump especially for pumping blood or other biological fluid comprises a generally conical housing in a circular base and conical side wall with a central fluid inlet at the apex of the housing and a peripheral outlet adjacent the base. A generally conical rotator rotatable in the housing comprises a central cone having a base and an apex and means on the cone for impelling flow of fluid from the inlet to the outlet of the housing upon rotation of the rotator. The rotator is rotatably supported in the housing by watch-type jewelled pivots of which one is located at the center of the base of the housing and the other is supported in the apex of the housing coaxially with the inlet by means of a spider which permits flow of fluid from the inlet into the housing. The rotor is rotatably supported solely by these two jewelled pivots and the pump is free of any seals or journal bearing exposed to the interior of the pump chamber. The rotator is driven in a manner known per se by providing magnets in the base of the central cone of the rotator in position to be driven by a rotating magnetic field at the base of the housing.

Advantages resulting from this construction lie essentially in the fact that the dynamic balance of the rotator is greatly improved in comparison with the single bearing arrangement and the absence of seals and friction bearings reduces considerably the production of heat and avoids hot spots and the risk of seal fragmentation. The use of watch-type jewelled pivots directly in contact with the circulating fluid ensures lubrication of the bearing by the fluid. As a side effect, the invention decreases the cost of the pump to a considerable extent.

BRIEF DESCRIPTION OF DRAWINGS

The nature, objects and advantages of the invention will be more fully understood from the following description of preferred embodiments shown by way of example in the accompanying drawings in which:

FIG. 4 is a view similar to FIG. 1 but showing another embodiment;

FIG. 5 is a view similar to FIG. 2 showing the embodiment of FIG. 4;

DESCRIPTION OF PREFERRED EMBODIMENTS

Figures 1, 2:
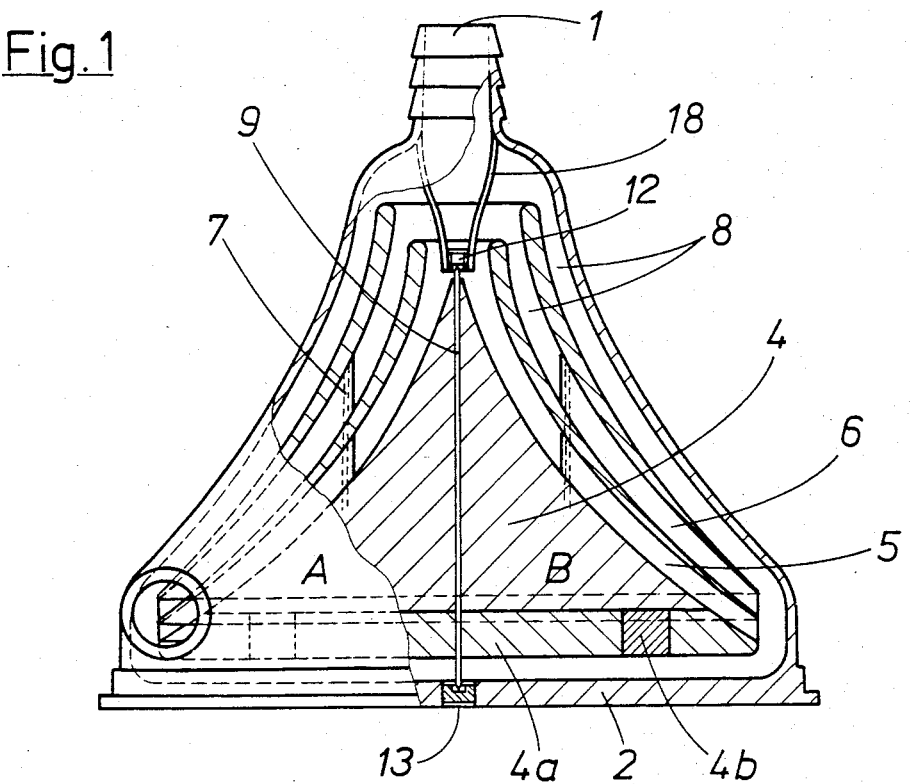
FIG. 1 is a view partially in side elevation and partially axial section of a pump constructed according to the teachings of this invention.
FIG. 2 is a top plan view with a portion broken away to show internal construction.

A pump for circulating blood or other body fluids such as fluid flow through the kidneys as illustrated in FIG. 1 comprises essentially a housing A in which a rotator B is rotatably mounted.

The housing A is substantially conical or bell-shaped and comprises at its top a suction inlet 1 and adjacent its base 2 a tangential delivery outlet 3. In operation the housing of the pump is secured against rotation by means of notches 2a in the periphery of the base 2. The housing is conveniently molded of suitable plastic material. While the housing is shown as being of integral construction it will be understood that the base is initially molded separately and is united with the side wall of the housing, for example by welding, adhesive or screw threads after the rotator has been inserted.

The rotator B is of a shape that matches the shape of the housing A and comprises a central cone 4 on which is provided means for impelling fluid from the inlet to the outlet upon rotation of the rotator. The impelling means is shown as comprising at least one downwardly outflaring skirt 5,6 interconnected by means of helical ribs or projections 7 constituting pump blades so as to provide between the central cone 4 and the skirt or skirts 5,6 one or more annular gaps 8 having an inlet at the top or suction end and an outlet at the level of the flat base of the rotator. The volume of the gap or gaps 8 is narrow enough to produce in conjunction with the helical configuration of the ribs 7 a suction proportional to the viscosity of the fluid and to the rotator speed.

The rotator is likewise conveniently molded of suitable plastic material and is preferably of integral construction with the gaps 8 formed by suitable coring.

The rotator B is rotatably supported in the housing A by an axial spindle or shaft 9 imbedded in the central cone 4. End portions 10 and 11 of the spindle 9 are provided with conical pivots 10a, 11a which cooperate with jewel-type bearings 12, 13 provided in the housing. Each of the bearings 12, 13 is provided with a jewel or like member 14, 15 made from a material capable of withstanding relatively high pressure and a continuous frictional contact with the pivots without heating. The pivots are lubricated by the fluid circulating in the pump. The upper pivot 12 is mounted in the apex of the housing by means of a spider or tripod-like member 18 which is streamlined in order not to interfere with the flow of fluid from the inlet 1 into the pump housing. The lower bearing 13 is mounted at the center of the base 2 of the housing.

Each of the jewels 14, 15 has a central cavity 16, 17 for receiving the conical ends 10a, 11a of the spindle 9.

Means is provided for micrometrically adjusting the position of the upper bearing 12 relative to the lower bearing 13 so as to provide correct bearing pressure between the bearings and the pivots. The adjusting means is shown as comprising a screw 19 which carries the upper bearing 12 and is screwed into a collar 18a of the spider 18 so that turning the screw 19 in one or the other direction will permit the position of the upper pivot in relation to the lower pivot to be varied as required. It will be seen that the screw 19 can be engaged by a screwdriver inserted through the inlet 1 so that the bearing can be adjusted after the pump is assembled.

The rotator is driven in rotation by means of a plurality of circumferentially spaced permanent magnets 4b which are embedded in the base portion 4a of the central cone 4. The magnets 4b cooperate with means provided below the base of the housing for producing a rotating magnetic field in known manner. Since the base 2 of the housing can be made relatively thin, the gap between the magnets 4b and the means for producing a rotating magnetic field can be quite small thereby providing a high efficiency.

Figure 6:
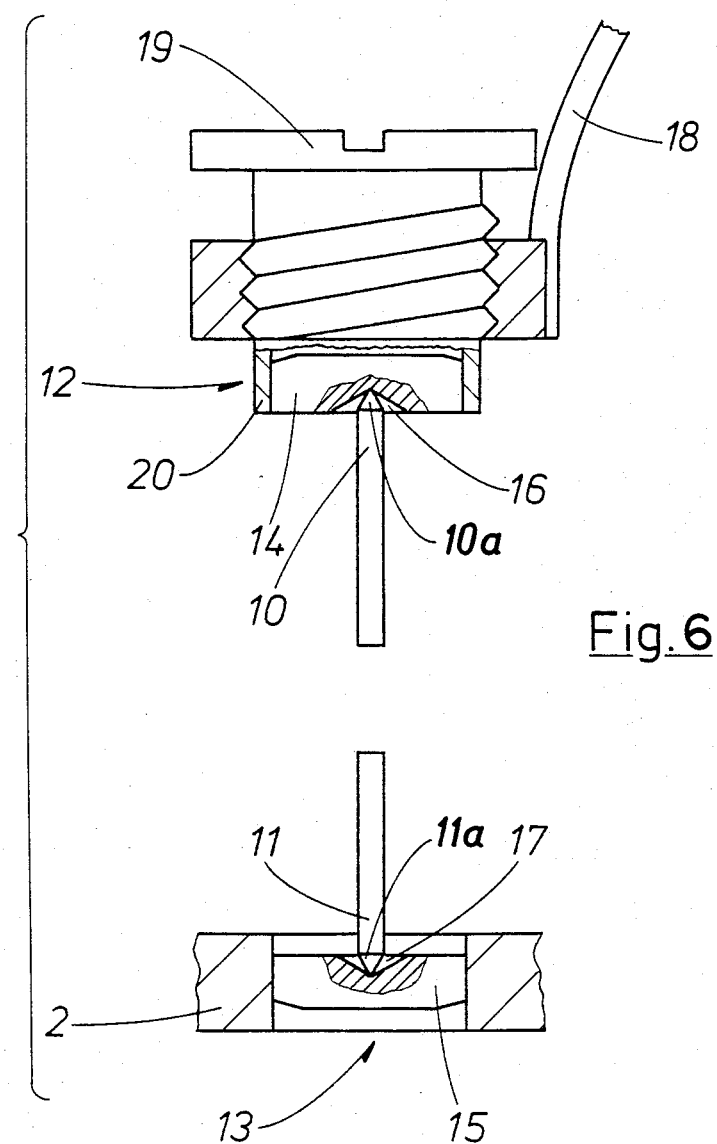
FIG. 6 is a view similar to FIG. 3 showing the embodiment of FIG. 4.

In FIGS. 4-6 there is shown another embodiment of the invention in which corresponding parts are designated by the same reference numerals. The embodiment shown in FIGS. 4-6 is in general the same as that of FIGS. 1-3 but differs in that the axial spindle 9 is replaced by two stub shafts 10 and 11 which are in axial alignment but spaced from one another. The upper stub shaft 10 has a conical end 10a engaging the jewel 14 of the upper bearing 12 while the lower stub shaft 11 has a concial end 11a engaging the jewel 15 of the lower bearing 13. By reason of the central cone 4 of the rotator B being molded of resilient plastic material, the construction illustrated in FIG. 6 has anti-shock characteristics which contribute to the ruggedness and dependability of the pump.

Figure 7:
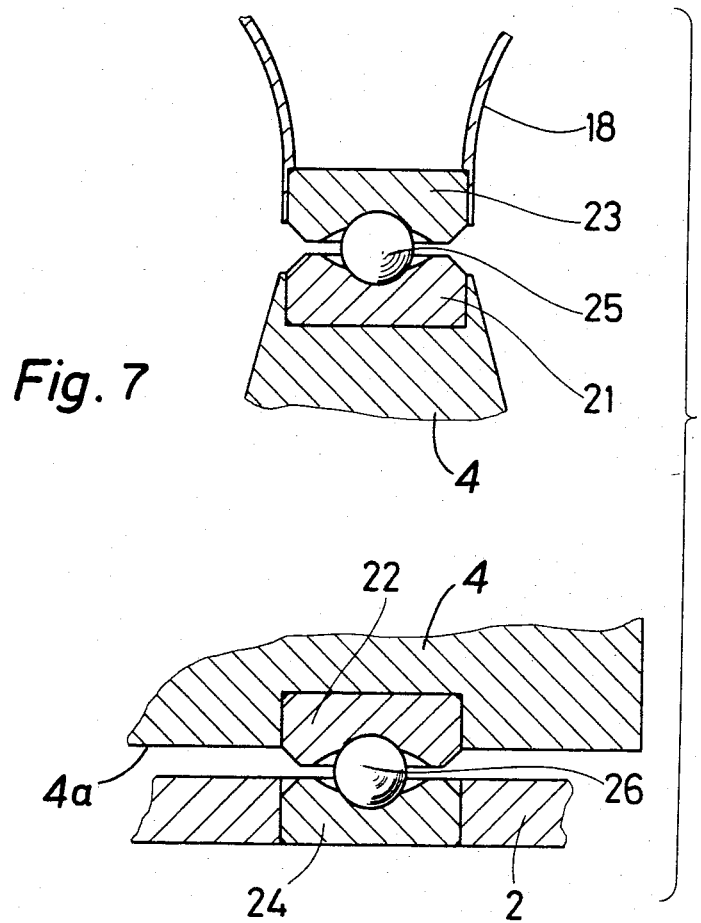
FIG. 7 is a schematic fragmentary axial section showing another embodiment of pivots rotatably supporting the rotator.

In FIG. 7 there is illustrated another embodiment of the invention in which the upper pivot of the rotator is provided by a single ball 25 received in a cavity of a jewel 21 mounted in the upper end of the central cone 4 of the rotator and in a cavity of a jewel 23 mounted in the tripod or spider 18 at the apex of the housing. The lower pivot of the rotator similarly comprises a single ball 26 received in a cavity of a jewel 22 mounted centrally in the base 4a of the central cone 4 of the rotator and a cavity in a jewel 24 mounted at the center of the base 2 of the housing A. The balls 25 and 26 are of small diameter and are of very hard material, for example tungsten carbide. The jewels 21-24 are of material capable of withstanding relatively high pressures and continuous frictional contact with the balls without material heating. As the material from which the central cone 4 of the rotator is molded has inherent resiliency, the construction shown in FIG. 7 has anti-shock characteristics. The upper jewel 23 can, if desired, be mounted by means of an adjusting screw as illustrated in FIG. 6.

Figure 8:
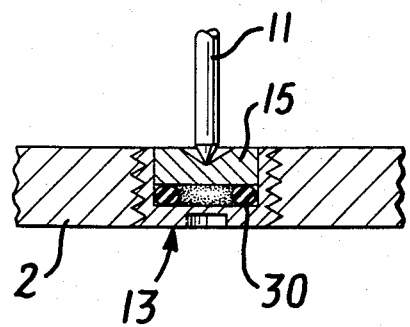
FIG. 8 is a fragmentary axial section showing an anti-shock pivot for the rotator.

If further shock resistance is desired, it can be provided by resiliently mounting one or both of the bearings in the housing by means of which the rotator is rotatably mounted. As illustrated by way of example in FIG. 8, the jewel 15 of the lower bearing 13 in the base 2 of the housing is resiliently mounted by means of a resilient member 30 which can, for example, be a spring washer but is shown as an O-ring of elastomeric material. With such construction, the bearing is cushioned against shocks. Moreover, if the upper bearing is adjustable as illustrated in FIG. 3, the adjustment of pressure is less critical.

Figure 3:
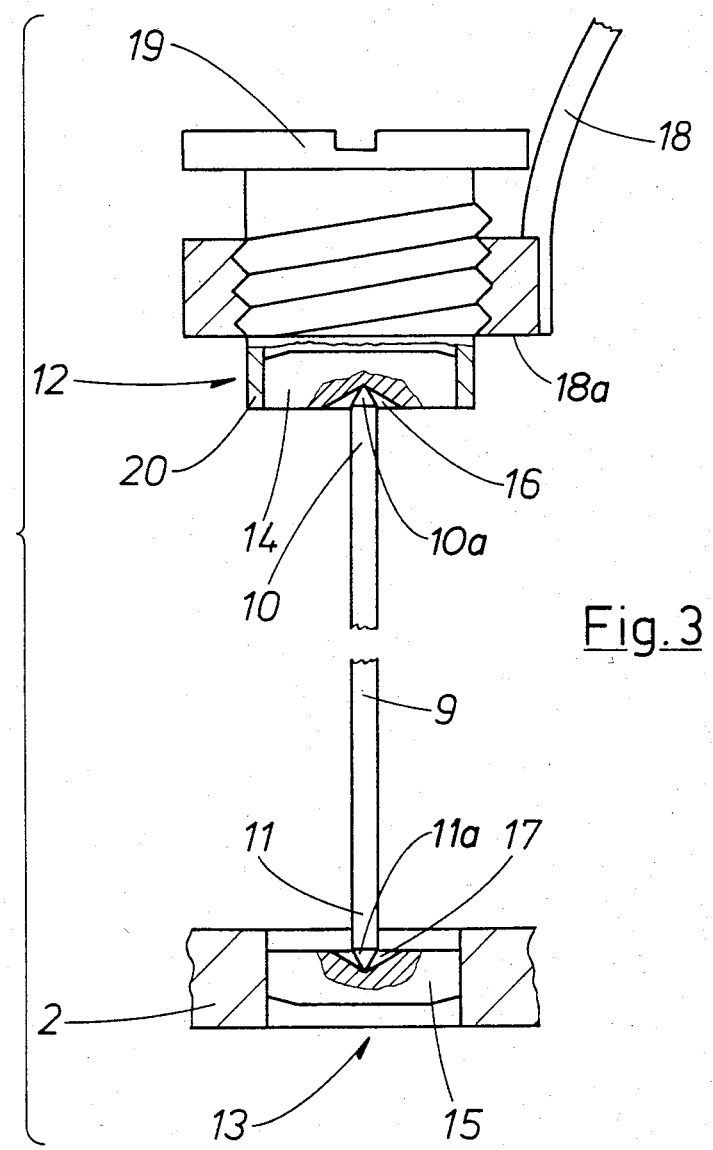
FIG. 3 is a fragmentary schematic view partially in side elevation and partially in axial section showing the pivots of the rotator.

It will be understood that the bearing construction shown in FIG. 3 can be reversed, i.e,. the bearings can comprise stub spindles mounted in the housing and engaging jewel bearings mounted on the central cone 4 of the rotator B. Such reversed construction is illustrated schematically in FIG. 9. A stub shaft 31 mounted in a collar portion 18a of the spider or tripod 18 has a conical lower end 31a received in a recess of a jewel bearing 32 mounted in the apex of the central cone 4 of the rotator B. The lower pivot comprises a stub shaft 33 mounted centrally in the base 2 of the housing A and having a conical upper end 33a received in a jewel bearing 34 which is molded centrally in the base 4a of the central cone 4 of the rotator. By reason of the resilience of the material of which the central cone 4 is formed, the construction illustrated in FIG. 9 has inherent shock resistance. It will be understood that the upper pivot can, if desired, be made adjustable as illustrated in FIG. 3.

Figure 9:
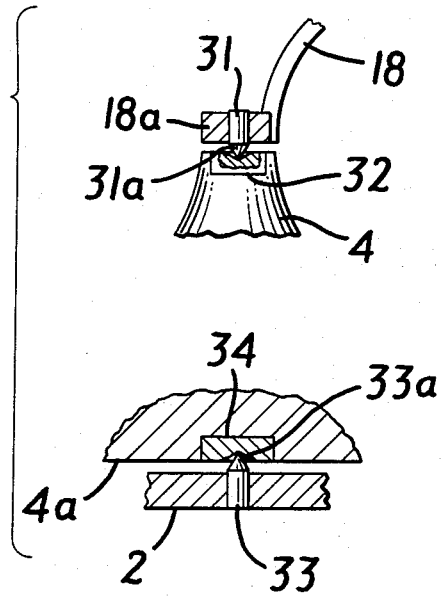
FIG. 9 is a schematic fragmentary view showing another embodiment of pivots for the rotator.

While several embodiments of the invention have been illustrated in the drawings, it will be understood that features of the invention can be combined in still other ways. For example the lower jewelled pivot of the rotator can be like that illustrated in FIG. 9 while the upper jewelled pivot can be like that illustrated in FIG. 6. Also one of the jewelled pivots may have a single ball as illustrated in FIG. 7 while the other has a conically pointed spindle as illustrated in FIG. 6 or FIG. 9. Still other variations will occur to those skilled in the art.

What we claim is:

1. A clinical centrifugal pump especially for pumping blood or other biological fluid, comprising:
    a generally conical housing having a circular base and conical side wall defining a generally concial pump chamber with a central fluid inlet at the apex of the housing and a peripheral outlet adjacent the base of the housing,
    a generally conical rotator rotatable in said housing and comprising a central cone having a base and an apex and means on said central cone for impelling flow from said inlet to said outlet upon rotation of said rotator,
    means rotatably supporting said rotator in said housing consisting of a first jewelled pivot at the center of the base of said housing and a second jewelled pivot supported in the apex of said housing coaxially with said inlet by a spider permitting flow of fluid from said inlet into said housing, said rotator being rotably supported solely by said jewelled pivots, and
    means for driving said rotator comprising spaced magnets in the base of said central cone in position to be driven by a rotating magnetic field at the base of said housing,
    said pump being free of any seals or journal bearing exposed to the interior of said pump chamber.

2. Clinical centrifugal pump according to claim 1, in which said flow impelling means comprises at least one flared skirt surrounding said central cone and helical blades connecting said skirt with said central cone.

3. Clinical centrifugal pump according to claim 1, in which said jewelled pivots comprise a central axial shaft in said rotator having opposite conical ends, a first jewel bearing in the center of the base of said housing receiving one conical end of said shaft and a second jewel bearing supported by said spider and receiving the opposite conical end of said shaft.

4. Clinical centrifugal pump according to claim 1, in which said central cone is of resilient plastic material and in which said first jewelled pivot comprises an axial stub shaft embedded in a lower portion of said central cone and having a pointed lower end and a first jewel bearing in the center of the base of said housing.

5. Clinical centrifugal pump according to claim 4, in which said second jewelled pivot comprises a second axial stub shaft embedded in an upper portion of said central cone and having a pointed upper end and a second jewel bearing supported in said housing by said spider.

6. Clinical centrifugal pump according to claim 1, in which each of said jewelled pivots comprises a first jewel bearing supported in said housing, a second jewel bearing on said rotator and a single ball between said two jewel bearings.

7. Clinical centrifugal pump according to any one of claims 3 to 6, in which one of said jewels bearings supported in said housing is micrometrically adjustable in a direction axial of said rotator to vary the pressure of engagement of said jewelled pivots.

8. Clinical centrifugal pump according to any one of claims 3 to 6, in which one of said jewel bearings is resiliently supported in said housing to provide anti-shock protection of said jewelled pivots.

9. Clinical centrifugal pumps according to claim 1, in which said first jewelled pivot comprises a central stub shaft projecting inwardly of said base of said housing and a jewel bearing mounted centrally in the base of said rotator.

10. Clinical centrifugal pump according to claim 1, in which said second jewelled pivot comprises an axial stub shaft supported in said housing by said spider and a jewel bearing mounted in the apex of said central cone of said rotator.

11. Clinical centrifugal pump according to claim 1, in which said magnets are set in a lower face of said base of said central cone in position to be driven by a rotating field applied below the base of the housing.

* * * * *